US008283589B2

(12) United States Patent
Janssens et al.

(10) Patent No.: US 8,283,589 B2
(45) Date of Patent: Oct. 9, 2012

(54) SORTING APPARATUS

(75) Inventors: Carlo Janssens, Londerzeel (BE); Geert Milis, Testelt (BE); Johan Calcoen, Wilsele (BE)

(73) Assignee: Key Technology, Inc., Walla Walla, WA (US)

( * ) Notice: Subject to any disclaimer, the term of this patent is extended or adjusted under 35 U.S.C. 154(b) by 51 days.

(21) Appl. No.: 12/928,063

(22) Filed: Dec. 1, 2010

(65) Prior Publication Data

US 2012/0138514 A1    Jun. 7, 2012

(51) Int. Cl.
*B07C 5/342* (2006.01)
(52) U.S. Cl. ......... 209/587; 209/576; 209/577; 209/939
(58) Field of Classification Search ................. 209/44.2, 209/576, 577, 587, 643, 644, 932, 939
See application file for complete search history.

(56) References Cited

U.S. PATENT DOCUMENTS

| | | | | |
|---|---|---|---|---|
| 4,630,736 A * | 12/1986 | Maughan et al. | ............. | 209/587 |
| 4,699,273 A * | 10/1987 | Suggi-Liverani et al. | .... | 209/580 |
| 5,165,068 A * | 11/1992 | Baldwin | ........................ | 348/104 |
| 5,172,005 A * | 12/1992 | Cochran et al. | ........... | 250/559.08 |
| 5,966,217 A * | 10/1999 | Roe et al. | ........................ | 356/402 |
| 6,078,018 A * | 6/2000 | Davis et al. | .................... | 209/580 |
| 6,097,493 A * | 8/2000 | Satake et al. | ................... | 356/609 |
| 6,410,872 B2 * | 6/2002 | Campbell et al. | .............. | 209/577 |
| 6,497,324 B1 * | 12/2002 | Doak et al. | ..................... | 209/522 |
| 6,603,103 B1 * | 8/2003 | Ulrich et al. | ................... | 250/205 |
| 8,116,554 B2 * | 2/2012 | Burton | ........................... | 382/141 |
| 2009/0032445 A1 * | 2/2009 | Doak et al. | ..................... | 209/587 |

* cited by examiner

*Primary Examiner* — Joseph C Rodriguez
(74) *Attorney, Agent, or Firm* — Paine Hamblen, LLP (57) ABSTRACT

A sorting apparatus is described and which includes an inspection station; a multiplicity of electromagnetic radiation emitters and detectors; an optical filter which is positioned in front of the electromagnetic radiation detectors, and which passes electromagnetic radiation having a given polarization; an ejector assembly positioned downstream from the inspection station for removing defective objects of interest which are identified; and a computer/controller for selectively energizing the electromagnetic radiation emitter, and detector, and rendering the ejector assembly operational to remove defective objects of interest, from a stream of objects of interest which have passed through an inspection station.

2 Claims, 7 Drawing Sheets

SORTING APPARATUS

TECHNICAL FIELD

The present invention relates to a sorting apparatus for use in sorting objects of interest such as row crops, and more specifically to a sorting apparatus having a greatly simplified design which facilitates the use of the invention in existing product processing lines and further provides an improved means for efficiently sorting given row crops.

BACKGROUND OF THE INVENTION

The respective inventors, and the assignee of the present application, have endeavored to develop a wide variety of different sorting assemblies which may be utilized to sort given objects of interest and particularly row crops of various types so as to identify defective products during the processing of same. As might be understood from even a casual review of the prior art, various food processors, and others, have continued to look for innovative ways to process large amounts of food products without the intervention of manual labor.

The prior art is replete with various sorter designs which are employed to image mass flow food products, detect defective product(s), and then remove the defective product(s) from the food product stream. All these designs have operated with varying degrees of success. However, they all have shortcomings which have detracted from their usefulness. For example, one of the shortcomings attendant with the prior art designs is that larger row crops, like ears of corn, are not readily processed using the high speed techniques and assemblies associated with many of the prior art teachings. In view of the size of the product, and its non-uniform shape, the prior art assemblies utilized for other mass flow food products such as what would be useful with peas, beans, peanuts and the like, are not useful with whole ears of corn, for example. Moreover, the ejection mechanisms employed with lightweight food products such as peas and beans and other similar row crops are not effective with a larger food product, such as an ear of corn. In addition to the foregoing, many of the prior art sorting devices have a relatively large factory footprint and are quite costly to install at existing manufacturing facilities.

Therefore, a sorting apparatus which avoids the shortcomings attendant with the prior art assemblies and practices which were utilized heretofore is the subject matter of the present invention.

SUMMARY OF THE INVENTION

A first aspect of the present invention relates to a sorting apparatus which includes an inspection station through which an object of interest to be inspected passes; an electromagnetic radiation emitter positioned in predetermined spaced relation relative to the inspection station, and which when energized emits electromagnetic radiation which is reflected from the object of interest, and back in the direction of the electromagnetic radiation emitter; an electromagnetic radiation detector positioned in close proximity to the electromagnetic radiation emitter, and which is configured to detect electromagnetic radiation emitted by the electromagnetic radiation emitter, and which is reflected from the object of interest, and wherein the electromagnetic radiation detector emits a signal when the electromagnetic radiation detector detects electromagnetic radiation which is reflected from the object of interest; a filter which is positioned in front of the electromagnetic radiation detector, and which passes the electromagnetic radiation which is reflected by the object of interest and delivers the passed electromagnetic radiation to the electromagnetic radiation detector; an ejector or ejection assembly for removing defective objects of interest at a location downstream relative to the inspection station; and a computer for selectively energizing the electromagnetic radiation emitter, and detector, and rendering the ejector assembly operational, and wherein the computer, receives and processes the signal generated by the electromagnetic radiation detector to identify defective objects of interest, and further causes the ejector assembly to operate to remove defective objects of interest from those objects of interest which have passed through the inspection station.

Another aspect of the present invention relates to a sorting apparatus which includes an inspection station through which an object of interest to be inspected passes, and wherein the inspection station has opposite first and second sides; a first electromagnetic radiation emitter positioned on the first side of the inspection station and which, when energized, emits polarized electromagnetic radiation toward the object of interest which is passing through the inspection station; a first electromagnetic radiation detector which is rendered operable to receive electromagnetic radiation which is perpendicularly offset relative to the emitted electromagnetic radiation, and which is positioned on the first side of the inspection station, and which is further operable to receive electromagnetic radiation which is reflected from the object of interest which is being inspected, and which had been previously emitted by the first electromagnetic radiation emitter; a first filter positioned in front of the first electromagnetic radiation detector and which is operable to pass reflected electromagnetic radiation which has a first predetermined polarization; a second electromagnetic radiation emitter positioned on the second side of the inspection station, and opposite to the first electromagnetic radiation emitter, and which, when energized, emits electromagnetic radiation which is reflected from the object of interest to be inspected, and which is passing through the inspection station; a second electromagnetic radiation detector positioned on the second side of the inspection station, and which is operable to receive electromagnetic radiation which is reflected from the object of interest which is being inspected, and which was previously emitted by the second electromagnetic radiation emitter; and a second filter positioned in front of the second electromagnetic radiation detector and which is operable to pass reflected electromagnetic radiation which has a second predetermined polarization which is the same as the first polarization.

These and other aspects of the present invention will be discussed in more detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

Figure 1:
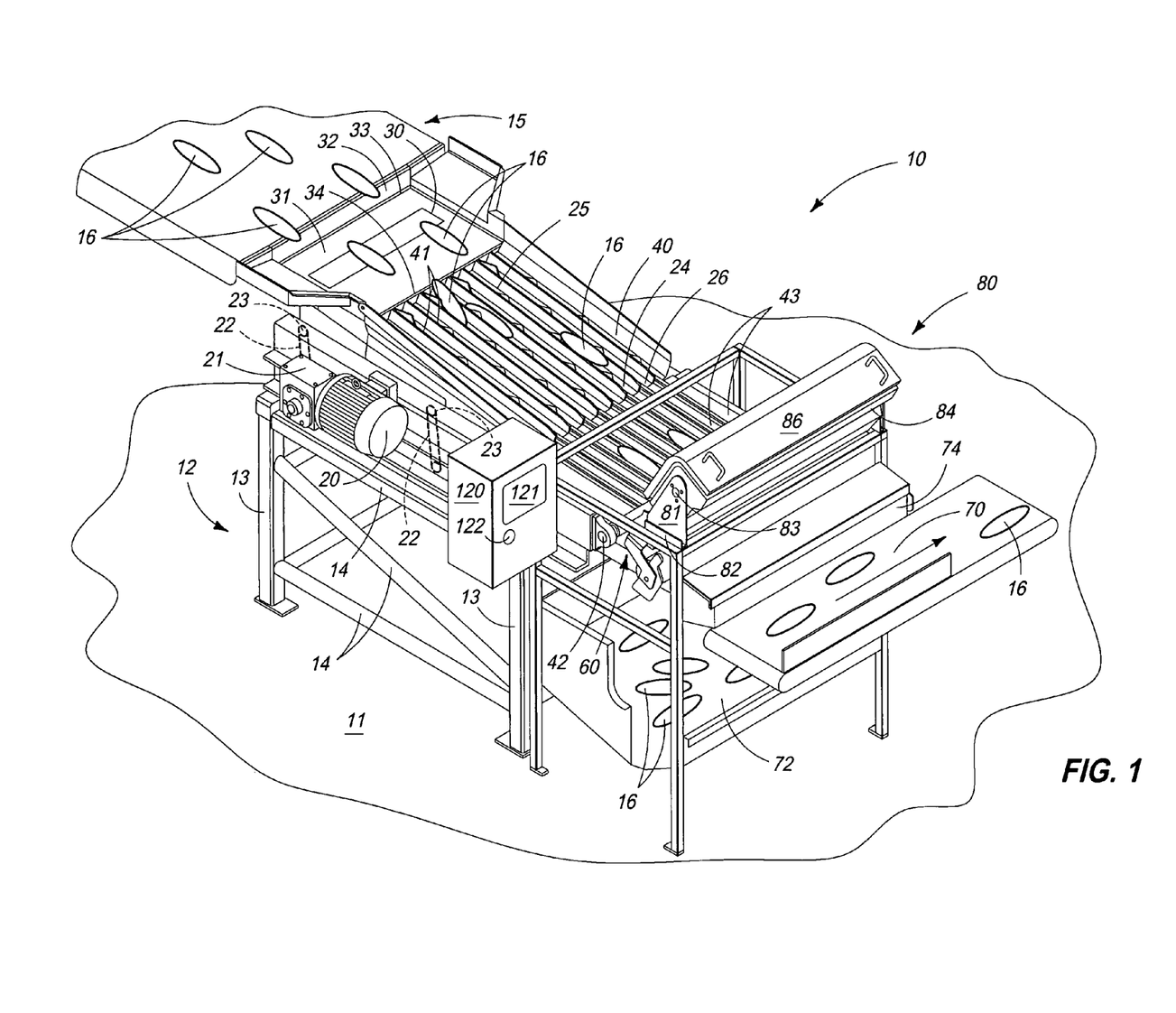
FIG. 1 is a perspective, side elevation view of one form of the sorting apparatus of the present invention.

Referring now to the drawings, the sorting apparatus of the present invention is generally indicated by the numeral 10 in FIG. 1 and following. It will be seen in that view that the sorting apparatus 10 of the present invention is positioned in spaced relation relative to a supporting surface 11, such as a factory floor, by a support frame which is generally indicated by the numeral 12. The support frame includes a multiplicity of vertically oriented support members 13, and a multiplicity of horizontal support member 14 which are joined to the vertical support members and which position the sorting apparatus 10 in spaced relation relative to the supporting surface 11. Additionally, it should be understood that while this supporting frame 12 is shown resting on an underlying supporting surface such as a factory floor, it will be appreciated that this same supporting frame may extend upwardly and be affixed to an overhead supporting surface such as a ceiling or the like, depending upon the processing environment in which it is installed. Further, as seen in FIG. 1, it will be understood that the sorting apparatus 10 is positioned in receiving relationship relative to an upstream piece of processing equipment 15, here illustrated, in part, as a husker which may be used in husking corn or the like, and which comprises the object of interest 16 which is delivered to the sorting apparatus 10 for further processing. While the object of interest 16 will be depicted hereinafter as an ear of corn, it will be appreciated that the principals of the present invention can be utilized to inspect various objects of interest and not just corn which is depicted in the drawings.

Figure 2:
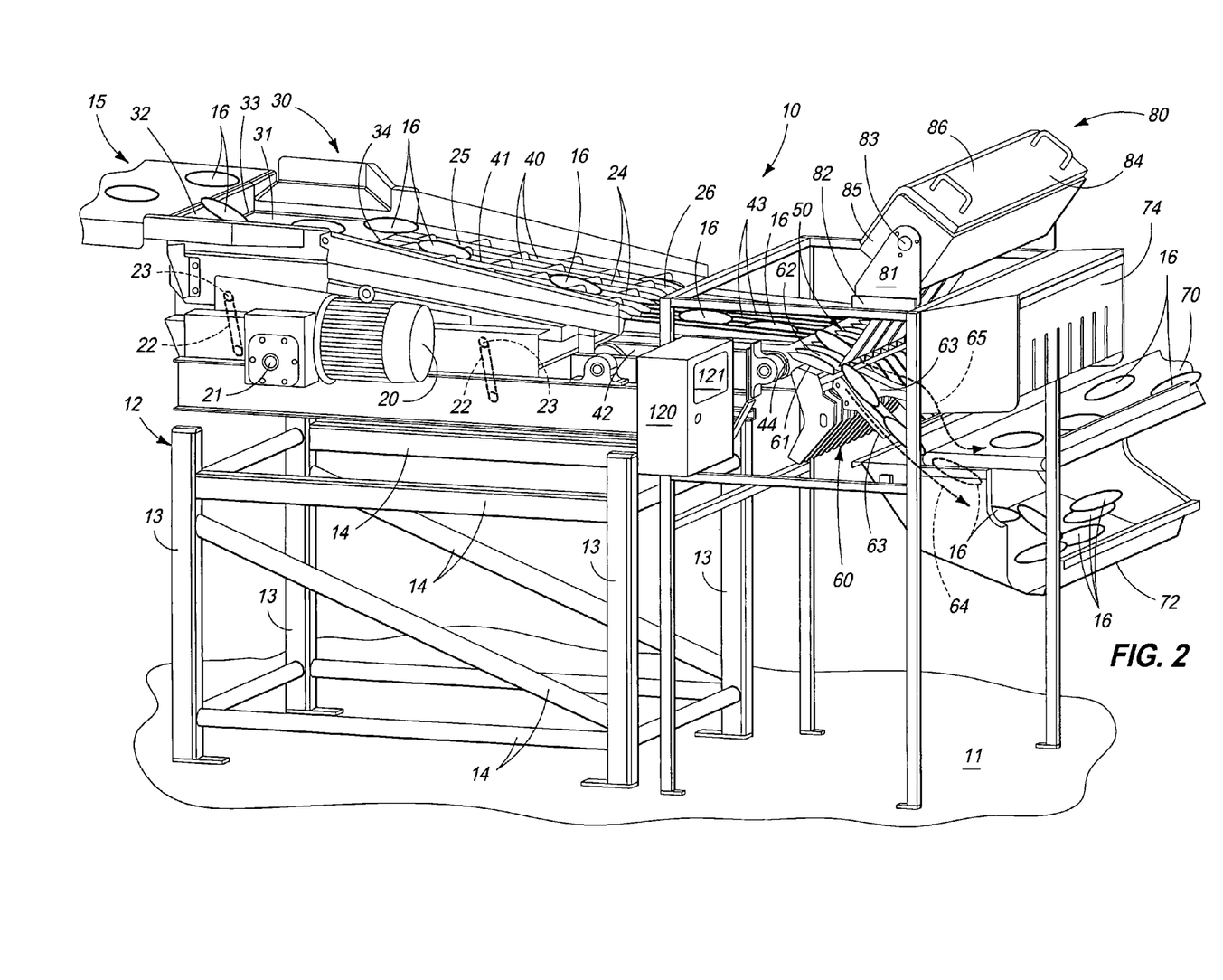
FIG. 2 is a side elevation view of one form of the sorting apparatus of the present invention.

Referring now to FIGS. 1 and 2, it will be understood that the present sorting apparatus 10 includes an electric drive motor 20 which is selectively energized by a source of power, and a control assembly which will be discussed in greater detail, hereinafter. The electric drive motor 20 which is mounted on the support frame 12 is coupled to an eccentric drive 21 of conventional design, and which is further mounted on the support frame 12. Additionally, mounted on the support frame 12 are a multiplicity of elongated resilient drive arms 22, also of conventional design. The respective drive arms 22 have a distal end 23 which supports or is otherwise mounted to a reciprocating bed 24. The electric drive motor 20, when energized in operable to impart motor force to the eccentric drive 21 which, in turn, is operable to cause the bed 24 to reciprocally move. This reciprocal movement causes the object of interest 16 to move between the first receiving end 25, and the opposite distal end 26 thereof. There are a multiplicity of prior art references which show the usefulness of using reciprocating conveyor beds of various designs for processing assorted products and other objects of interest. In the arrangement as seen in the drawings, the eccentric drive 21, when energized by the electric motor 20 causes the reciprocating bed 24 to reciprocate at a rate of about 300 strokes per minute. Each stroke has a length of about 1 inch or 25 mm.

Referring still FIGS. 1 and 2 it will be seen that the sorting apparatus of the present invention 10 includes a receiving or redistribution platform of portion 30 which is disposed in receiving relationship relative to the upstream equipment as illustrated in FIG. 1. The receiving or redistribution platform or portion 30 is operable to receive the objects to be inspected 16, here depicted as ears of corn, that have been previously husked from the upstream processing equipment 15. The receiving or redistribution platform 30 has an upwardly facing supporting surface 31 which allows the objects of interest 16 to be redistributed across the width of the reciprocating bed 24 which is positioned downstream relative thereto. The redistribution platform has a multiplicity of upwardly facing sidewalls 32 which confines the objects of interest 16 on the upwardly facing supporting surface 31. Further, the upwardly facing supporting surface 31 has a proximal edge 33 which is located in receiving relation relative to the upstream processing equipment 15, and an opposite distal edge 34, which is located adjacent to the first end 25 of the reciprocating bed 24.

Referring now to FIG. 1, the sorting apparatus 10 of the present invention includes a multiplicity of troughs which are generally indicated by the numeral 40, and which are mounted on the reciprocating bed 24 as earlier described. The several troughs are operable to define a multiplicity of lanes 41. The respective troughs 40 or the defined lanes 41 receive the objects to be inspected 16 from the receiving or redistribution platform 30, and are operable to align the respective objects of interest 16 here depicted as ears of corn, into the individual lanes 41 for travel between the first and second ends 25 and 26 of the reciprocating bed 24. The multiplicity of troughs also have the effect of causing the object to be inspected, here the corn, to be positioned in a single layer. Positioned at the second end 26 of the reciprocating bed 24 is a short endless, accelerating conveyor 42 of conventional design. The accelerating conveyor is about 24 inches long and delivers the objects of interest 16, here illustrated as the aligned ears of corn, at an appropriate spacing for optimal scanning and subsequent downstream treatment by the assemblies which will be discussed in greater detail, hereinafter. As seen in FIG. 1, a series of rigid guide members 43 are mounted in spaced relationship over the accelerating conveyor belt 42 to maintain the objects of interest, here, ears of corn, in alignment, for singulization through the inspection and ejection regions of the sorting apparatus 10 as will be described, below. The endless accelerating conveyor 42 has a distal end 44 (FIG. 2) which delivers the singulated objects of interest 16, (the ears of corn), to the ejector assembly which will be discussed in greater detail, below.

Positioned in downstream receiving relation relative to the distal end 44 of the endless accelerating conveyor 42 is an inspection station which is generally indicated by the numeral 50. The inspection station 50 is located between an ejection station 60, and a vision module 80 which will be discussed in greater detail in the paragraphs which follow. As discussed briefly, above, the ejection station 60, as noted above, is located downstream relative to the reciprocating bed 24. The ejection station 60 includes a first portion 61 which comprises a multiplicity of stationary receiving shoes 61 which are generally concavely shaped, and which are oriented in a coaxial relationship relative to the multiplicity of defined lanes 41 as provided by the reciprocating bed 24. These concavely shaped shoes 61 which comprise the first portion of the ejection station 60 supports the various objects of interest 16 in a given orientation relative to the inspection station 50 so they may be imaged for purposes of determining whether the respective objects of interest 16 have any defects. As seen in FIG. 2, these respective, fixed, first portion shoes 61 are angled downwardly so that the objects of interest 16 may continue to flow or move, under the influence of gravity, downwardly so as to be received onto a multiplicity of movable deflectors which are generally indicated by the numeral 63. The moveable deflectors 63 are also concavely shaped in order to support the singulated objects of interest for movement along either first or second paths of travel 64 or 65, respectively, depending upon the determined status of the respective objects of interest, that is, whether it is acceptable 64, or includes a defect 65. The respective moveable deflectors 63 are driven or moved so as to direct the objects of interest 16 into the first or second path of travel 64 or 65 by individual pneumatic cylinders (not shown), and which are energized or activated by a computer control which will be discussed in greater detail in the paragraphs which follow.

As seen in FIG. 2, it will be understood that a reject or cross-feed conveyor is positioned in receiving relation relative to the second path of travel 65 and is operable to receive objects of interest 16 which have been identified as being defective and then transport them for additional reprocessing. In the illustrated form of the invention 10 as shown, a reject or defective object of interest 16, here depicted as an ear of corn, might include ears of corn which have not been successfully husked in the upstream process. In this scenario, the ear of corn is then delivered onto the cross-feed conveyor 70 and is transported back to a rehusk shoot (not shown) which is positioned upstream of the sorting apparatus 10 for reprocessing. Further, acceptable objects of interest 16 move along a first path of travel 64 and then move to a downstream processing methodology (not shown).

Referring now to FIGS. 3-7, it will be understood that the present sorting apparatus 10 includes a novel vision module which is generally indicated by the numeral 80, and which is positioned in the inspection station 50. The vision module 80, which is rotatable about its longitudinal axis, is supported in spaced relationship relative to the objects of interest 16 that are received on the first portion 61 of the ejection station 60 by means of a frame 81. The frame 81 has a base portion 82 which is fixed on at least one of the horizontal members 14 which forms part of the support frame 12. Still further, the frame 81 mounts a rotatable support 83 which is fixed to the vision module housing 84. The vision module housing 84 has a first major side 85 and an opposite second side or end 86.

Figure 3:
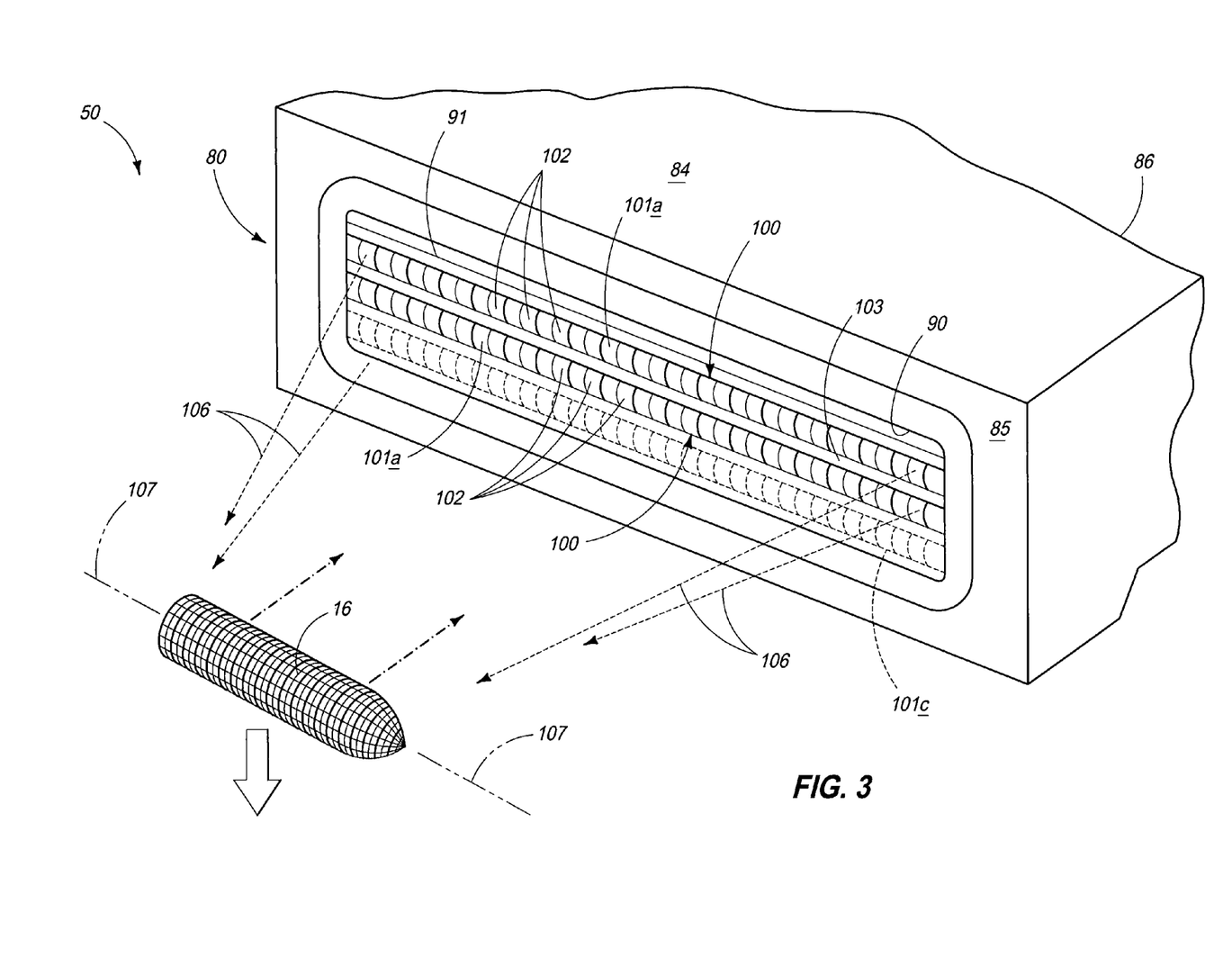
FIG. 3 is a fragmentary, perspective, side elevation view of one feature of the present invention.
Figure 6:
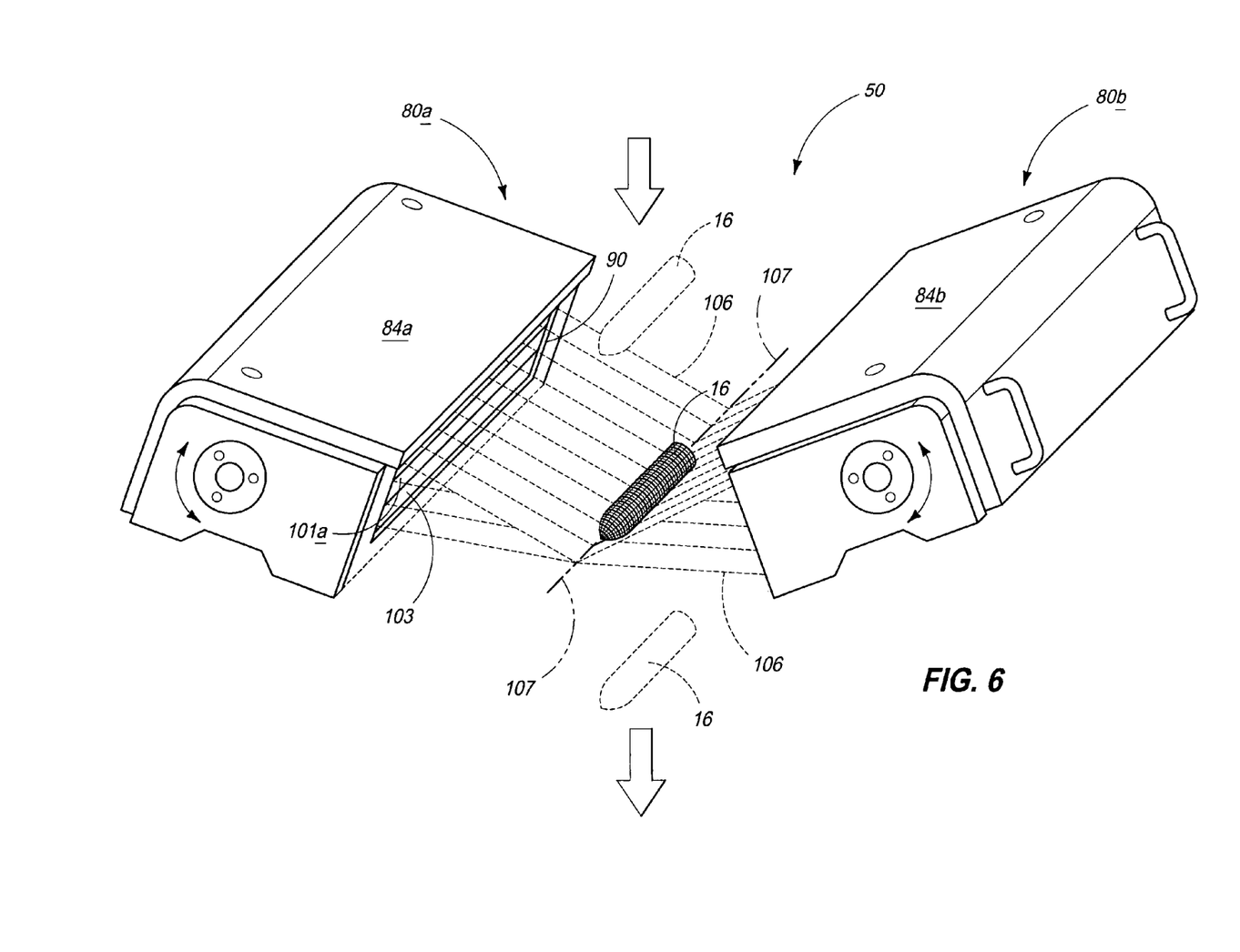
FIG. 6 is a greatly simplified, schematic, perspective view of one feature of the present invention.

As seen by reference to FIGS. 3 and 6, the vision module 80 and more specifically, the vision module housing 84 has an aperture 90 formed in the first side 85, and which leads to an internal cavity (not shown). The housing 84 further has a transparent cover panel 91 which occludes the aperture 90, and which protects the internal cavity of the vision module 80. As seen most clearly by reference to FIG. 7, the vision module 80 encloses a processing board 92 which is operable to energize the components of the vision module 80. The processing board which is depicted includes multiple electrical inputs 93A and B. The processing board further has power outputs 94 which are electrically coupled to a multiplicity of electromagnetic radiation emitters here shown as a pair of light emitting diode bars 101 which will be discussed in greater detail, below. Additionally, the processing board 92 includes inputs and outputs 95 that are electrically coupled to a plurality of electromagnetic radiation detectors 104. These structures will be discussed in greater detail in the paragraphs which follow.

Figure 5:
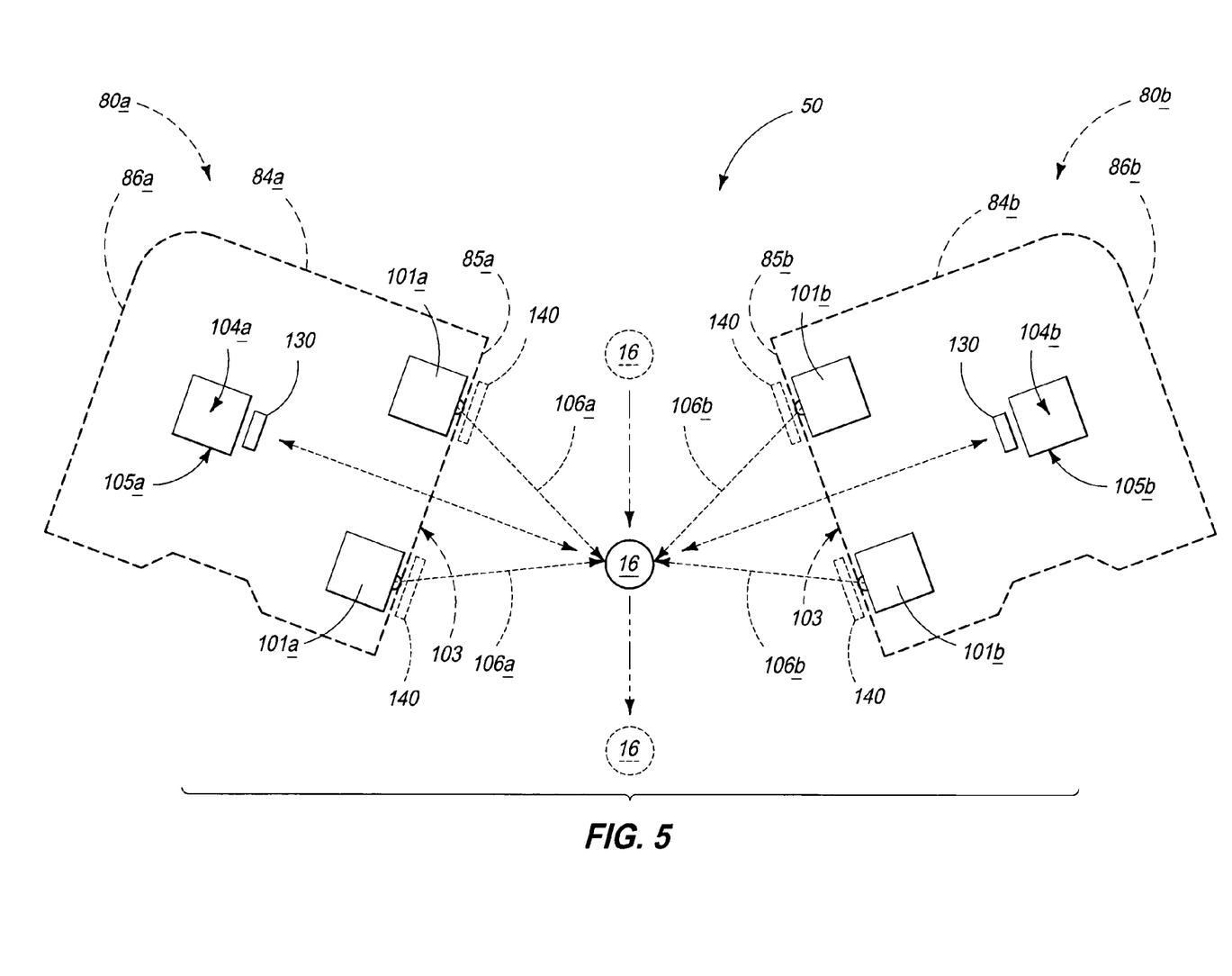
FIG. 5 is a greatly simplified, schematic view of one feature of the present invention.
Figure 7:
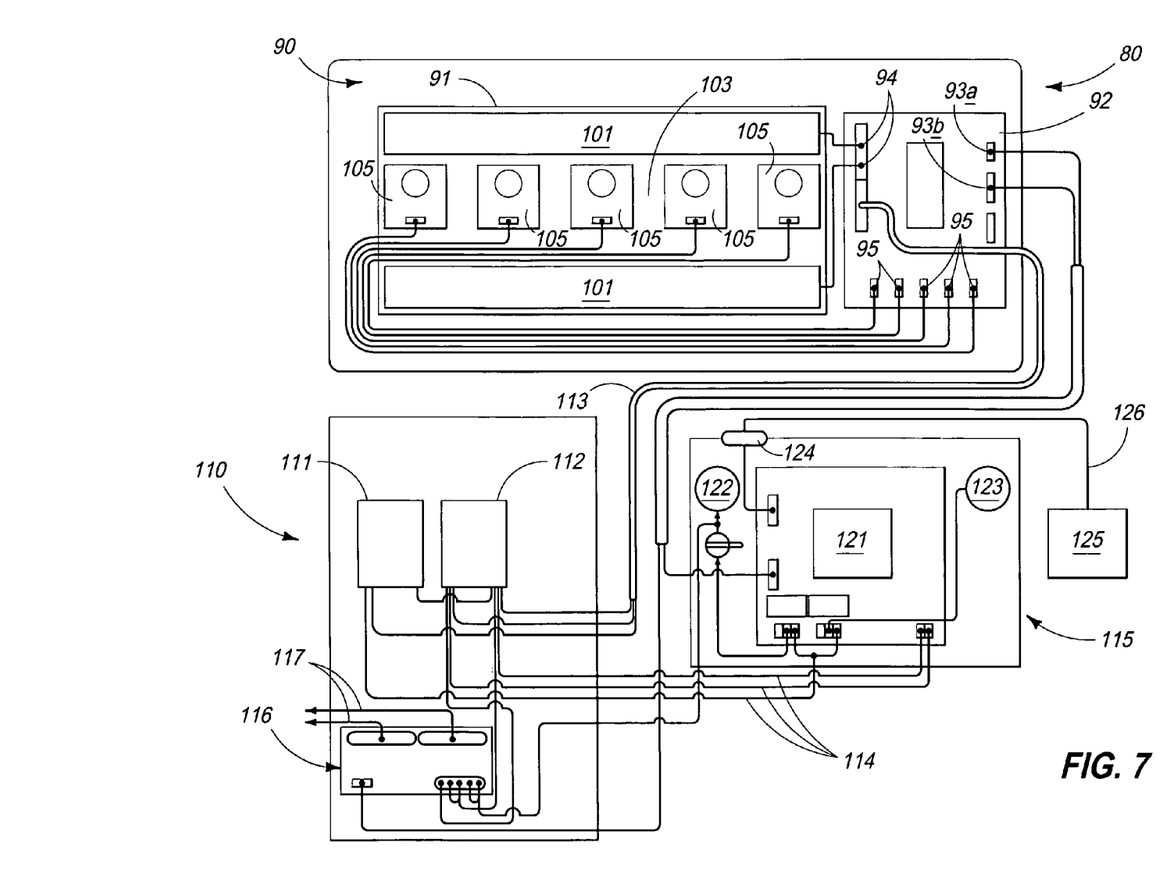
FIG. 7 is a greatly simplified, schematic view of several features of the present invention and which may find usefulness when used with the structures seen in FIGS. 1 and 2, respectively.

In the drawings (FIG. 3) of the present application, it will be seen that the vision module 80 includes a plurality of individual electromagnetic radiation emitters which are generally indicated by the numeral 100. The electromagnetic radiation emitters are positioned in predetermined spaced relation relative to the inspection station 50, and which, when energized, emits visible, invisible or combinations of invisible or visible electromagnetic radiation which is reflected from the object of interest 16 and back in the direction of the electromagnetic radiation emitters 100. As seen in the present drawings, the plurality of electromagnetic radiation emitters 100 are formed into a pair of light emitting diode lighting bars 101. The pair of light emitting diode bars 101 include a multiplicity of individual light emitting diodes 102 which are oriented in a general linear orientation and substantially parallel to each other. Additionally, as seen in FIGS. 3 and 7, a gap or space 103 is formed therebetween the pair of LED lighting bars 101. Positioned within that gap or space 103 is a plurality of electromagnetic radiation detectors 104A, B, here depicted as individual industrial line scan cameras 105A, B which are electrically coupled to the processing board 93 as shown in FIG. 7. As seen in FIGS. 3 and 5, the respective pair of LED lighting bars are tilted or oriented, when installed within the vision module housing 84, such that the respective LED lighting bars 101 emit visible, invisible, or a combination of visible and invisible light along individual lines of sight 106A, B which converge to a location 107 within the inspection station 50 through which the object of interest 16 passes. This is best illustrated by reference to FIG. 5 and FIG. 6, respectively. Therefore, it will be seen in the drawings that the sorting apparatus 10 includes a plurality of electromagnetic radiation emitters in the form of two banks of light emitting diodes 101 which are oriented in a parallel, linear arrangement, and which are spaced a given distance apart and wherein the electromagnetic radiation detectors 104A-B here indicated as individual cameras 105A-B are located in the space or gap 103 which is defined between the pair of light emitting diode bars or banks 101. Additionally, other light emitting diodes 101C (FIG. 3 only) may be located below the light emitting diode bars 101 and which emit a background light which can only be seen from the opposite side of the inspection station 50. The plurality of electromagnetic radiation emitters 100, when selectively energized (or strobed), emits a multiplicity of bands of visible, invisible or combinations of visible, and invisible light which is then reflected by the object of interest 16. As should be understood, the visible or invisible light which is emitted from the individual light emitting diodes 102 is polarized in a given plane or orientation and then is directed towards the object of interest 106 along the converging lines of sight 106 and then reflected back in the direction of the plurality of electromagnetic radiation detectors 104. As this emitted light strikes, and then is reflected back in the directions of the electromagnetic radiation detectors 104A, B some of the reflected light is scattered or diffused in such a manner that the polarization of the reflected light is changed to a polarization which is now perpendicularly offset relative to the plane of polarization of the light as was originally emitted. As should be understood, and in the invention as seen in FIG. 5, it will be appreciated that the electromagnetic radiation 106 emitted from one vision module 80 which is positioned on one side of the inspection station 50 and that of the other vision module positioned on the opposite side of the inspection station 50 will have the same polarization. Further, in this arrangement, the electromagnetic radiation detectors in each vision module 80 will each be rendered operable to only detect reflected light which has a polarization which is cross polarized, circular polarized or otherwise offset by about 90 degrees from the polarization of the emitted light such that electromagnetic radiation detectors will not detect the presence of the emitted electromagnetic radiation. The reason for this polarization offset will be discussed in the paragraphs which follow. In the arrangement as seen in the drawings, the plurality of electromagnetic radiation detectors 104 comprise a multitude of line scan cameras (here depicted as 5) which detect the light (visible and/or invisible) which is reflected from the object of interest 16 passing through the inspection station 50.

In the arrangement as seen in FIG. 1 and following, and regardless of the form of the invention, the electromagnetic radiation which is emitted is periodically pulsed by the processing module or board 92 and is directed toward the object of interest 16. This module or board 92 includes a microprocessor for controlling the operation of the sorter 10. The electromagnetic radiation emitters 100 emit electromagnetic radiation which is in the same of different bands of visible, invisible, or a combination of visible and invisible light. Still further, and in another form of the invention 10, the plurality of electromagnetic radiation emitters 100 may be selectively energized in a given sequence to emit visible and/or invisible electromagnetic radiation having predetermined wavelengths. This selective energizing may include short periods of time where no electromagnetic radiation is emitted and during which the sorter 10 measures the ambient light levels in the inspection station 50, and then makes lighting corrections based on that ambient light measurement. The plurality of electromagnetic radiation emitters 100, as seen, are oriented in a linear array which has a length dimension of about 900 mm. Further, the individual electromagnetic radiation detectors may comprise a multitude of micro-board line-scan cameras (here seen as 5), and which can each operably image at least about 150 mm. of the inspection station 50 through which the object of interest 16 passes. In another form of the invention, the electromagnetic radiation detectors may comprise a plurality of InGsAs cameras, and the plurality of electromagnetic radiation emitters, when energized, may emit near infra-red electromagnetic radiation.

As seen by reference to FIG. 7, the sorting apparatus 10 is supplied electrical power from a power supply box which is generally indicated by the numeral 110. The power supply box 110 encloses a first power supply 111 which generates and then supplies 24 volt, 10 Amp power to the various components discussed, above. Further, a second power supply 112 is provided in the power supply box 110, and which generates a 5 volt, 10 Amp output. Both sources of power may be provided by means of an electrical conduit 113 to the processing board 92 or, in the alternative, by means of an electrical conduit 114 to a user interface which is generally indicated by the numeral 115. Further, enclosed within the power supply box is a valve driver board 116 for actuating the downstream movable deflectors 63 which were earlier described. As noted earlier, the plurality of deflectors 63 are moved between various positions to send the object of interest 16, which has been inspected, into selected first or second paths of travel 64 and 65 by means of pneumatically energized cylinders (not shown) which are controlled by a fast acting pneumatic valve which is under computer control. In this regard, the power supply box, and more specifically the valve driver board 116 has valve driver electrical outputs 117 which are electrically couple with the respective pneumatic cylinders (not shown) in order to move the downstream movable deflectors 63 to a given orientation so as to direct the objects of interest 16 between the first path of travel and the second path of travel 64 and 65, respectively.

Referring now to FIGS. 1 and 7, it will be seen that a housing 120 is positioned to the side of, and adjacent to, the sorting apparatus 10 as seen in FIG. 1, and which encloses the user interface 115 previously mentioned in the paragraph, immediately, above. In this regard, the housing 120 encloses the user interface 115 so that an operator (not shown) may set various operational parameters for the sorting apparatus 10. As seen in FIG. 7, the user interface 115 includes a conventional touch screen 121 which provides various pieces of information which are useful for an operator to consider when operating the sorter apparatus 10. The touch screen 121 is accompanied by a valve control switch 122 which again is operably coupled with the multiplicity of pneumatic cylinders (not shown) which individually control the operation of the multiplicity of movable deflectors 63 as earlier described. As seen in FIG. 7, an input/output connector or connection 124 is provided. Still further, a computer/controller 125 may be coupled to the sorter 10 for purposes of uploading or downloading relevant files for use by the processing module 92. The processing module 92 controls the operation of the electromagnetic radiation emitters, detectors and the ejection assembly, all of which were discussed, above. An electrical conduit 126 couples the computer/controller 125 with the computer input/output connection 124 in a manner well known in the art. The computer (processing module or board 92) receives and interprets the signals received from the electromagnetic radiation detectors and then identifies defective products or objects of interest 16 once identified by the computer, and then causes individual deflectors 63 to move to an orientation such that the defective object of interest 16 is directed along the path of travel 65, and acceptable product along the path of travel 64.

Figure 4:
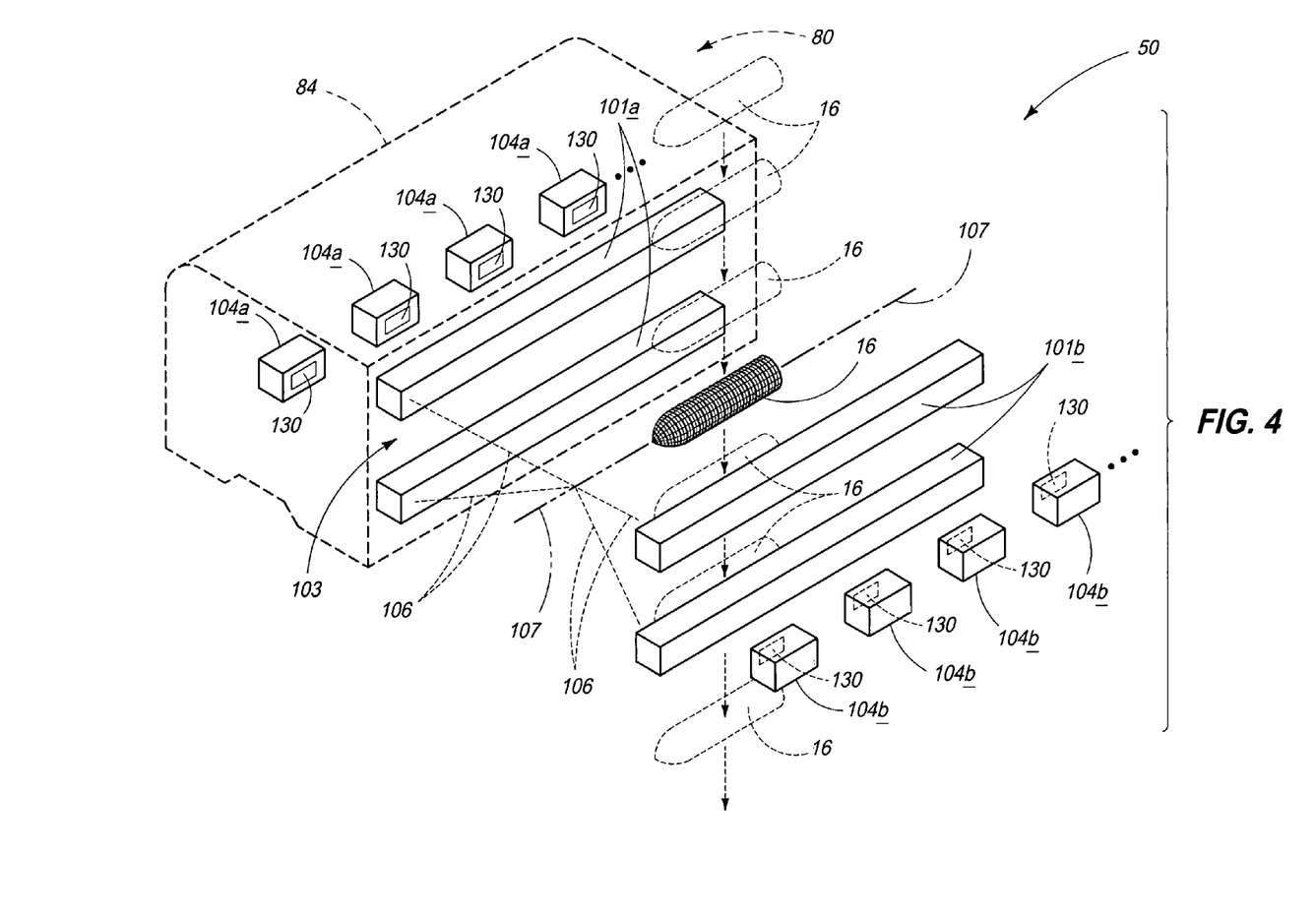
FIG. 4 is a greatly simplified, schematic view of one feature of the present invention.

Referring now to the rather simplified schematic drawing of FIG. 4, where the object of interest to be inspected is shown as an ear of corn, it will be understood that the present invention 10 includes a multiplicity of optical filters 130 which are positioned in front of the respective plurality of electromagnetic radiation detectors 104. The plurality of filters are individually operable to act as a polarizing element so as to allow electromagnetic radiation to pass which is polarized in a given plane. More specifically, it should be understood that in the arrangement of the invention as shown, the plurality of electromagnetic radiation emitters 100, when energized, emits electromagnetic radiation which is directed towards and reflects from the object of interest 16. The electromagnetic radiation emitted by the individual electromagnetic radiation emitters is polarized in a given plane, and the optical filters 130 are provided and which allow only emitted electromagnetic radiation which has been reflected by the object of interest, and which now has a polarization different from that which was emitted to pass through the respective optical filters 130 and be received by the plurality of electromagnetic radiation detectors 104 positioned therebehind. Only a portion of the light reflected from the object of interest 16 has this characteristic. In the present invention 10, the optical filters 130 only allow reflected light which is now in a plane which is about 90 degrees offset relative to the plane in which the light was emitted to pass. As earlier discussed, the individual electromagnetic radiation detectors comprise individual line scan cameras 105 of conventional design. Still further, it should be understood that the multiplicity of individual filters 130 which are positioned on the opposite sides of the inspection station 50 have the same polarization. Therefore, light emitted from one side of the inspection station 50 cannot be detected by the multiplicity of electromagnetic radiation detectors 104 located on the opposite side of the inspection station 50. This allows for the individual electromagnetic radiation emitters 100 positioned on opposite sides of the inspection station 50 to be energized substantially simultaneously while not creating optical interference for the electromagnetic radiation detectors 104 which are positioned on the opposite side of the inspection station 50. In the arrangement as illustrated, the electromagnetic radiation emitters 100 which are provided are operable to generate electromagnetic radiation which is polarized in the same plane. In other instances, electromagnetic radiation emitters 100 may be provided which do not generate polarized emissions. If this is the case, an optional, optical polarizing assembly or other filter 140 may be provided and which is positioned between the electromagnetic radiation emitter 100 and the object of interest. This specific optical polarizing assembly 140 which is shown only in phantom lines in the drawing, would then allow electromagnetic radiation to pass only in the given plane of orientation.

OPERATION

The operation of the described embodiment of the present invention is believed to be readily apparent and is briefly summarized at this point.

Referring now to the drawings, it will be seen that the sorting apparatus 10 of the present invention includes an inspection station 50 through which an object of interest 16 to be inspected passes. An electromagnetic radiation emitter 100 is positioned in predetermined spaced relation relative to the inspection station 50, and which, when energized, emits electromagnetic radiation 106 which is polarized in a given plane and which is reflected from the object of interest 16, and back in the direction of the electromagnetic radiation emitter 100. When the emitted electromagnetic radiation is reflected, a portion of the electromagnetic radiation returns which has a polarization which is perpendicular relative to that polarization in which it was originally emitted. An electromagnetic radiation detector 104 is positioned in close proximity to the electromagnetic radiation emitter 100, and which is configured to detect electromagnetic radiation 105 which was previously emitted by the electromagnetic radiation emitter 100, but which is reflected from the object of interest 16, and which further has the polarization which is substantially perpendicular relative to the emitted polarization. The electromagnetic radiation detector 104 emits a signal when the electromagnetic radiation detector detects electromagnetic radiation which is reflected from the object of interest 16, and which is passed by the filter 130. The filter 130 is positioned in front of the electromagnetic radiation detector 104, and passes the electromagnetic radiation 106 which is reflected by the object of interest 16 and delivers the passed electromagnetic radiation to the electromagnetic radiation detector 104. An ejector assembly 60 is provided for removing defective objects of interest 16 at a location downstream relative to the inspection station 50. Further, a computer/controller 92 is provided for selectively energizing the electromagnetic radiation emitter 100, and detector 104, and rendering the ejector assembly 60 operational, and wherein the computer/controller 92, receives and processes the signal generated by the electromagnetic radiation detector 104 to identify defective objects of interest 16, and further causes the ejector assembly 60 to operate in a manner to remove defective objects of interest 16 from those objects of interest 16 which have passed through the inspection station 50. The computer 125 is further provided to collect data from the sorter 10, and then use the data as an external tool so as to facilitate the optimization of the sorter 10.

In the arrangement as seen in the drawings, the inspection station 50 supports the objects of interest 16 in a given orientation relative to the inspection station 50. Still further, the electromagnetic radiation emitter 100, and detector 104 comprise a plurality of electromagnetic radiation emitters and detectors. In the drawings as provided with this application, the plurality of electromagnetic radiation emitters 100 comprise two banks or bars 101 of light emitting diodes which are oriented in a parallel, linear arrangement. The pair of light emitting diode banks 101 are spaced a given distance apart. Still further, the plurality of electromagnetic radiation detectors 104 are located in the space or gap 103 which is defined between the pair of light emitting diode banks 101. In the arrangement as seen in the drawings, the plurality of electromagnetic radiation emitters 100, when selectively energized, emits a multiplicity of bands of visible, invisible, or combinations of visible and invisible light 106, which is then reflected by the object of interest 16. As earlier discussed, the emission or light 106 which is emitted is polarized in a given plane of orientation, and the filter 130 which is provided comprises an optical filter which is operable to pass only the light which has a polarization which is perpendicular to the plane of light or emission which is emitted by the plurality of electromagnetic radiation emitters 100 which have been energized. As earlier noted, and in another form of the apparatus, an optical polarizing assembly 140 is positioned in front of the two banks of light emitting diodes 101 and which polarizes the electromagnetic radiation emitted by the energized light emitting diode banks into a predetermined plane of orientation for use in the invention. As seen in FIG. 5, the invention 10 includes plurality of electromagnetic radiation detectors 104, which is here illustrated as at least 5 line scan cameras 105, and which detects the light or other emission which is passed by the optical filter 130, and which produces the electrical signal which is sent to the computer/controller 125 for further processing. Of course the present apparatus could be rendered operable with any number of cameras.

As should be understood from a study of the drawings, the invention includes two forms. The first one is seen in FIGS. 1 and 2 whereby the invention 10 is provided with one vision module 80 which is operable to inspect objects of interest 16 passing through the inspection station 50; and a second form of the invention as best seen by reference to FIGS. 5 and 6 which includes two vision modules 80 which are positioned on opposite sides of an inspection station 50, and through which an object of interest 16 passes by means of gravity. Therefore, in the second form of the invention, a second plurality of electromagnetic radiation emitters 100, and detectors 104 as well as the filters 130 are located on the opposite side of the inspection station 50. The object of interest 16 passes between the first mentioned electromagnetic radiation emitters and detectors 101 and 104, respectively, and the second plurality of electromagnetic radiation detectors located on the opposite side of the inspection station 50. Similar to the first form of the invention, the second plurality of electromagnetic radiation emitters comprise two banks of light emitting diodes 101 which are oriented in a parallel, linear arrangement, and wherein the pair of light emitting diode banks are spaced a given distance apart. The second plurality of electromagnetic radiation detectors 104 are located in the space 103 which is defined between the pair of light emitting diode banks 101. The electromagnetic radiation 106 which is generated by the second plurality of electromagnetic radiation emitters is polarized in a given plane which is the same as the plane of polarization of the emitted electromagnetic radiation generated by the first mentioned electromagnetic radiation emitters. The second filters 130 pass the light reflected by the object of interest passing through the inspection station 50, and which has a plane of polarization which is substantially perpendicular to that plane which was emitted. In both forms of the invention, the electromagnetic radiation which is emitted is periodically pulsed. Still further, the line scan cameras 105 which are provided in one form of the invention are monochromatic, and further the light emitted by the electromagnetic radiation emitters may include two different colors which are both emitted at substantially the same time. As seen in the drawings, and in the second form of the invention as seen in FIGS. 5 and 6, the first and second plurality of electromagnetic radiation emitters 101 which are located on opposite sides of the inspection station 50 emit electromagnetic radiation 106 which is oriented so as to converge on a region 107 of the inspection station 50 through which the object of interest 16 passes. In the form of the invention as seen in FIGS. 5 and 6, the respective optical filters 130 pass emitted electromagnetic radiation which is oriented in planes which are offset by about 90 degrees relative to that emitted by the electromagnetic radiation emitters 101. In one possible form of the invention, the filter 130 may comprise a circular polarizing filter. This is typically useful in the form of the invention as seen in FIGS. 1 and 2. Further, with respect to FIGS. 5 and 6, it will be understood that the first and second electromagnetic radiation emitters which are located on the opposite side of the inspection station 50 include individual electromagnetic radiation emitters which, when energized, emits a visible color light which can be detected by the respective first and second electromagnetic radiation detectors 104 which are located on the opposite sides of the inspection station relative to the electromagnetic radiation emitters being energized. Further, and in the form of the invention as seen in FIGS. 5 and 6, at least one of the electromagnetic radiation emitters 101 emits a colored light which comprises a backlight reference which may be detected by the electromagnetic radiation detector 104 located on the opposite side of the inspection station 50 relative to the electromagnetic radiation detector being energized. This backlight reference is indicated at 101C, and is only shown in FIG. 3. The light emitted by this backlight reference 101C can be seen by the electromagnetic radiation detectors 104 which are located on the opposite side of the inspection station 50.

In the arrangement as seen in the drawings, the first and second electromagnetic radiation emitters 100 located on opposite sides of the inspection station 50 comprise a plurality of electromagnetic radiation emitters which are oriented in a linear array which has a length dimension of about 900 millimeters, and the first and second electromagnetic radiation detectors 104 comprise 5 micro-board line scan cameras which are each operable to image at least 150 millimeters of the inspection station 50 through which the object of interest 16 passes. In some applications like the sorting of corn 16 as seen in FIGS. 1 and 2, this object of interest 16 (corn) is oriented in a preferred direction by the lanes 41, and the moveable deflectors are coaxially aligned with these lanes 41. In one possible form of the invention, the first and second electromagnetic radiation detectors comprise a plurality of InGaAs cameras, and the first and second electromagnetic radiation emitters 100 comprise a plurality of emitters, which when energized, emit near-infrared electromagnetic radiation. As earlier discussed, the invention is operable whereby the first and second electromagnetic radiation emitters 100 and detectors 104 located on opposite sides of the inspection station 50 can be energized simultaneously without creating any substantial optical interference to the oppositely positioned electromagnetic radiation detectors 104. In the form of the invention as shown, the micro-board line scan cameras 105 operate at substantially the same scan rate in order to provide a signal which is provided to the computer 92 which acts upon same in order to control the downstream ejection of defective objects of interest 16 by means of the ejector assembly 60.

Therefore, it will be seen that the present invention provides a convenient means for sorting objects of interest 16 in a highly expeditious manner while avoiding the detriments associated with the individual practices and devices utilized heretofore. The present invention is highly efficient, allows for illumination and imaging of an object of interest in a manner which allows for the detection of abnormalities in a highly efficient manner and further provides a convenient ejector assembly for removing defective objects of interest from a stream of product in a manner not possible heretofore.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A sorting apparatus, comprising:
   an inspection station through which an object of interest passes in a predetermined orientation, and wherein the object of interest is supported, and travel through the inspection station on a downwardly declining, and underlying supporting surface;
   a pair of spaced bars of light emitting diodes, and wherein the respective bars of light emitting diodes are oriented in parallel, spaced, linear relation, one relative to the other, and wherein a space is defined between the respective pair of light emitting diode bars, and wherein the respective spaced bars of light emitting diodes, when selectively energized, individually emit electromagnetic radiation in a multiplicity of visible, invisible, or combinations of visible and invisible bands, and wherein the emitted electromagnetic radiation from the respective pair of spaced bars of light emitting diodes is directed in a converging orientation onto, and is reflected from, the object of interest which is passing through inspection station on the underlying supporting surface;
   an optical polarizing assembly positioned in front of the pair of bars of the light emitting diodes, and which passes, and then polarizes the emitted electromagnetic radiation which is generated by the respective bars of the light emitting diodes into a first polarization, and wherein the polarized electromagnetic radiation is directed to, and reflected from, one side of the object of interest, and wherein the reflected electromagnetic radiation includes both the electromagnetic radiation which has the first polarization, and reflected electromagnetic radiation which has a polarization which is different from the first polarization;
   a multitude of line scan cameras located between the pair of spaced bars of light emitting diodes;
   a filter which is positioned in front of the respective multitude of line scan cameras, and which is operable to pass the reflected electromagnetic radiation which has a polarization which is different from the first polarization, and be received by the multitude of line scan cameras, and wherein the reflected electromagnetic radiation having both the first polarization, and the polarization different from the first polarization, and which is reflected from the object of interest, passes through the space defined by the respective pair of spaced banks of light emitting diodes, and wherein the multitude of line scan cameras individually emit an electrical signal when the electromagnetic radiation having a polarization different from the first polarization is reflected by the object of interest and is detected;
   an ejector assembly for removing a defective object of interest at a location which is downstream relative to the inspection station, and which includes a moveable deflector which is positioned in gravity receiving, downstream relation relative to the supporting surface which supports the object of interest in the inspection station, and which directs the object of interest into different courses of travel; and a computer for selectively energizing and rendering operable, the respective bars of light emitting diodes, and the individual multitude of line scan cameras, and further rendering the moveable deflector of the ejector assembly operational, and wherein the computer receives, and processes the electrical signal generated by the multitude of line scan cameras to identify a defective object of interest, and further causes the moveable deflector of the ejector assembly to operate and remove the defective object of interest by directing the defective object of interest into one of the courses of travel.

2. A sorting apparatus, comprising:

an inspection station through which an object of interest passes in a predetermined orientation, and wherein the object of interest is supported, and travels through the inspection station on a downwardly declining, and underlying supporting surface;

a pair of spaced bars of light emitting diodes, and wherein the respective bars of light emitting diodes are oriented in parallel, spaced, linear relation, one relative to the other, and wherein a space is defined between the respective pair of light emitting diode bars, and wherein the respective spaced bars of light emitting diodes, when selectively energized, individually emit a first polarized electromagnetic radiation in a multiplicity of visible, invisible, or combinations of visible and invisible bands, and wherein the emitted first polarized electromagnetic radiation from the respective pair of spaced bars of light emitting diodes is directed in a converging orientation onto, and is reflected from one side of the object of interest which is passing through inspection station on the underlying supporting surface, and wherein the reflected electromagnetic radiation includes both the electromagnetic radiation which has the first polarization, and reflected electromagnetic radiation which has a polarization which is different from the first polarization;

a multitude of line scan cameras located between the pair of spaced bars of light emitting diodes;

a filter which is positioned in front of the respective multitude of line scan cameras, and which is operable to pass the reflected electromagnetic radiation which has a polarization which is different from the first polarization, and be received by the multitude of line scan cameras, and wherein the reflected electromagnetic radiation having both the first polarization, and the polarization different from the first polarization, and which is reflected from the object of interest, passes through the space defined by the respective pair of spaced banks of light emitting diodes, and wherein the multitude of line scan cameras individually emit an electrical signal when the electromagnetic radiation having a polarization different from the first polarization is reflected by the object of interest and is detected;

an ejector assembly for removing a defective object of interest at a location which is downstream relative to the inspection station, and which includes a moveable deflector which is positioned in gravity receiving, downstream relation relative to the supporting surface which supports the object of interest in the inspection station, and which directs the object of interest into different courses of travel; and a computer for selectively energizing and rendering operable, the respective bars of light emitting diodes, and the individual multitude of line scan cameras, and further rendering the moveable deflector of the ejector assembly operational, and wherein the computer receives, and processes the electrical signal generated by the multitude of line scan cameras to identify a defective object of interest, and further causes the moveable deflector of the ejector assembly to operate and remove the defective object of interest by directing the defective object of interest into one of the courses of travel.

* * * * *